United States Patent
Friedel et al.

(10) Patent No.: US 10,766,025 B2
(45) Date of Patent: Sep. 8, 2020

(54) PREPARATION AND USE OF COPPER CONTAINING HYDROGENATION CATALYST

(71) Applicant: SHELL OIL COMPANY, Houston, TX (US)

(72) Inventors: Frank Peter Friedel, Leuna (DE); Wolfgang Dirk Lose, Leuna (DE); Andreas Klemt, Leuna (DE)

(73) Assignee: Shell Oil Company, Houston, TX (US)

( * ) Notice: Subject to any disclaimer, the term of this patent is extended or adjusted under 35 U.S.C. 154(b) by 10 days.

(21) Appl. No.: 15/580,482

(22) PCT Filed: Jun. 7, 2016

(86) PCT No.: PCT/EP2016/062855
§ 371 (c)(1),
(2) Date: Dec. 7, 2017

(87) PCT Pub. No.: WO2016/198379
PCT Pub. Date: Dec. 15, 2016

(65) Prior Publication Data
US 2018/0141032 A1    May 24, 2018

(30) Foreign Application Priority Data
Jun. 9, 2015    (EP) .................................... 15171095

(51) Int. Cl.
| | | |
|---|---|---|
| *B01J 37/00* | (2006.01) | |
| *B01J 37/03* | (2006.01) | |
| *B01J 37/04* | (2006.01) | |
| *B01J 37/08* | (2006.01) | |
| *B01J 37/18* | (2006.01) | |
| *B01J 21/06* | (2006.01) | |
| *B01J 23/72* | (2006.01) | |
| *C07C 29/145* | (2006.01) | |
| *B01J 35/02* | (2006.01) | |
| *B01J 37/06* | (2006.01) | |
| *C07C 33/22* | (2006.01) | |

(52) U.S. Cl.
CPC ............. *B01J 37/031* (2013.01); *B01J 21/06* (2013.01); *B01J 23/72* (2013.01); *B01J 35/023* (2013.01); *B01J 37/0009* (2013.01); *B01J 37/0036* (2013.01); *B01J 37/04* (2013.01); *B01J 37/06* (2013.01); *B01J 37/08* (2013.01); *B01J 37/18* (2013.01); *C07C 29/145* (2013.01); *C07C 33/22* (2013.01); *B01J 2231/643* (2013.01); *C07C 2523/72* (2013.01)

(58) Field of Classification Search
CPC ...... B01J 37/0009; B01J 37/031; B01J 37/04; B01J 37/08; B01J 37/18; B01J 21/06; B01J 23/72
See application file for complete search history.

(56) References Cited

U.S. PATENT DOCUMENTS

| | | | | |
|---|---|---|---|---|
| 2,891,094 A | * | 6/1959 | Karkalits, Jr. ............ | B01J 23/72 564/420 |
| 2,939,844 A | * | 6/1960 | Ellinger .................... | B01J 23/72 502/154 |
| 3,209,033 A | * | 9/1965 | Shotts ....................... | B01J 23/72 568/400 |
| 3,741,888 A | * | 6/1973 | Chun et al. ............. | C10G 27/04 208/191 |
| 3,741,889 A | * | 6/1973 | Chun et al. ............. | C10G 27/04 208/191 |
| 4,184,982 A | * | 1/1980 | Schroeder ................ | B01J 23/70 502/234 |

* cited by examiner

*Primary Examiner* — Cam N. Nguyen
(74) *Attorney, Agent, or Firm* — Charles W. Stewart

(57) ABSTRACT

The invention relates to a process for preparing a catalyst, which comprises: mixing a copper salt containing solution with a silicate salt containing composition resulting in a precipitated solid; and subjecting the precipitated solid to a temperature in the range of from 150 to 500° C. Further, the invention relates to a copper containing catalyst obtainable by said process. Still further, the invention relates to a hydrogenation process wherein such copper containing catalyst is used, more in particular a process wherein methyl phenyl ketone is hydrogenated into methyl phenyl carbinol.

23 Claims, No Drawings

US 10,766,025 B2

PREPARATION AND USE OF COPPER CONTAINING HYDROGENATION CATALYST

PRIORITY CLAIM

The present application is the National Stage (§ 371) of International Application No. PCT/EP2016/062855, filed Jun. 7, 2016, which claims priority from European Patent Application No. 15171095.1 filed Jun. 9, 2015 incorporated herein by reference.

FIELD OF THE INVENTION

The present invention relates to a process for preparing a copper containing catalyst, more in particular a copper containing hydrogenation catalyst; to a copper containing catalyst obtainable by said process; and to a hydrogenation process wherein such copper containing catalyst is used, more in particular a process wherein methyl phenyl ketone is hydrogenated into methyl phenyl carbinol.

BACKGROUND OF THE INVENTION

It is known to use copper containing catalysts in all kinds of processes, more in particular in hydrogenation processes.

For example, EP0714877A2 discloses a process for producing α-phenylethyl alcohol by hydrogenation of acetophenone, which uses a copper-based catalyst containing at least one alkaline earth metal carbonate and/or at least one alkali metal compound. Said acetophenone corresponds to methyl phenyl ketone (MPK); and said α-phenylethyl alcohol corresponds to methyl phenyl carbinol (MPC; 1-phenylethanol).

It is an objective of the present invention to provide a process for preparing a copper containing catalyst, wherein the catalyst thus obtained can be used in a hydrogenation process, for example a process wherein methyl phenyl ketone is hydrogenated, resulting in a relatively high conversion and/or selectivity.

SUMMARY OF THE INVENTION

Surprisingly it was found that a highly active and selective, copper containing hydrogenation catalyst can be prepared by a process which comprises:

mixing a copper salt containing solution with a silicate salt containing composition resulting in a precipitated solid; and subjecting the precipitated solid to a temperature in the range of from 150 to 500° C.

Accordingly, the present invention relates to a process for preparing a catalyst, which comprises the above-mentioned steps.

In a further embodiment of the process of the present invention, the above steps are followed by:

mixing the thermally treated precipitated solid with a shaping aid containing suspension;

shaping the mixture thus obtained resulting in shaped bodies; and subjecting the shaped bodies to a temperature in the range of from 150 to 500° C.

Further, the present invention relates to a copper containing catalyst obtainable by said process.

Still further, the present invention relates to a hydrogenation process wherein said copper containing catalyst is used, more in particular a process wherein methyl phenyl ketone is hydrogenated into methyl phenyl carbinol.

DETAILED DESCRIPTION OF THE INVENTION

Thus, the catalyst preparation process of the present invention comprises the following steps:

mixing a copper salt containing solution with a silicate salt containing composition resulting in a precipitated solid; and subjecting the precipitated solid to a temperature in the range of from 150 to 500° C. resulting in a thermally treated precipitated solid.

While the process of the present invention is described in terms of "comprising", "containing" or "including" one or more various described steps, it can also "consist essentially of" or "consist of" said one or more various described steps. The same applies in relation to compositions, gas streams and so on "comprising", "containing" or "including" one or more various described components.

In the present invention, the copper salt containing solution is preferably an aqueous solution. Further, the copper salt from said solution may be any copper salt. The copper salt may be a nitrate, sulfate, chloride or organic acid salt of copper. Preferably, the copper salt is copper nitrate or an organic acid salt of copper, most preferably copper nitrate. A suitable organic acid salt of copper is copper acetate.

Preferably, the amount of copper in the catalyst obtainable by the process of the present invention is of from 40 to 95 wt. %, more preferably 50 to 80 wt. %, calculated as copper(II) oxide (CuO) based on total weight of the catalyst.

In the present invention, the silicate salt containing composition may comprise a silicate salt containing solution and/or a silicate salt containing suspension. That is to say, the silicate salt containing composition may comprise a silicate salt containing solution; or a silicate salt containing suspension; or a silicate salt containing solution and a silicate salt containing suspension. In the present invention, the silicate salt containing composition is preferably an aqueous composition, that is to say an aqueous solution and/or suspension. In the present invention, the silicate salt containing solution is preferably an aqueous solution. Further, the silicate salt from said composition, that is to say solution and/or suspension, may be any silicate salt. Preferably, the silicate salt comprises an alkali metal silicate salt, preferably a sodium silicate salt, and/or an earth alkaline metal silicate salt, preferably a calcium silicate salt. More preferably, the silicate salt comprises an alkali metal silicate salt, preferably a sodium silicate salt. In case the silicate salt comprises an alkali metal silicate salt, the silicate salt containing composition preferably comprises a silicate salt containing solution. In case the silicate salt comprises an earth alkaline metal silicate salt, the silicate salt containing composition preferably comprises a silicate salt containing suspension.

Most preferably, the silicate salt comprises an alkali metal silicate salt, preferably a sodium silicate salt, and further, the precipitated solid, resulting from mixing the copper salt containing solution with the silicate salt containing composition, that is to say solution and/or suspension, is mixed with an earth alkaline metal silicate salt, preferably a calcium silicate salt, before subjecting the mixture thus obtained to a temperature in the range of from 150 to 500° C.

In the present invention, an earth alkaline metal silicate salt, preferably a calcium silicate salt:

may be mixed with the copper salt containing solution and/or the silicate salt containing composition before and/or during mixing the copper salt containing solution with the silicate salt containing composition; and/or may be mixed with the precipitated solid, resulting from mixing the copper salt containing solution with the silicate salt containing composition, before subjecting the mixture thus obtained to a temperature in the range of from 150 to 500° C.; and/or may be mixed with the thermally treated precipitated solid, resulting from subjecting the precipitated solid to a temperature in the range of from 150 to 500° C., with the proviso that the mixture thus obtained is subjected to a temperature in the range of from 150 to 500° C.

That is to say, in the present invention, the earth alkaline metal silicate salt may be added in one or more of the above-described ways. Preferably, the earth alkaline metal silicate salt is added by mixing with the precipitated solid, resulting from mixing the copper salt containing solution with the silicate salt containing composition, before subjecting the mixture thus obtained to a temperature in the range of from 150 to 500° C. Further, the earth alkaline metal silicate salt may be added as an earth alkaline metal silicate salt containing suspension, preferably an aqueous suspension. Further, preferably, the silicate salt from the silicate salt containing composition that is mixed with the copper salt containing solution, comprises an alkali metal silicate salt, preferably a sodium silicate salt.

Preferably, in any one of the aforementioned cases wherein a calcium silicate salt is used in a suspension, for example an aqueous suspension, the pH of such suspension is 7 or higher, more preferably of from 7 to 9. At such pH, advantageously, substantially no calcium carbonate is formed by mixing the calcium silicate salt containing suspension with a basic solution comprising for example sodium hydroxide and/or sodium carbonate. It is preferred not to have calcium carbonate in the final catalyst because in an acidic environment carbon dioxide is formed from the carbonate. This is detrimental to catalyst stability.

In the present invention, the precipitation is preferably carried out in the presence of a base. This may be achieved by adding a base to the mixture of the copper salt containing solution and the silicate salt containing composition, that is to say solution and/or suspension, or to the silicate salt containing composition, that is to say solution and/or suspension before mixing with the copper salt containing solution. Further, the base may comprise one or more bases selected from the group consisting of sodium hydroxide, sodium carbonate, sodium hydrogen carbonate, potassium hydroxide, potassium carbonate and potassium hydrogen carbonate. Preferably, sodium carbonate or a mixture of sodium hydroxide with sodium carbonate is used.

The amount of base is preferably such that substantially all of the copper salt is precipitated. This may be achieved by using such amount of base that a pH of 7 or greater, or 7.5 or greater, or 8 or greater, is achieved in the dispersion (or slurry) that results from mixing the copper salt containing solution with the silicate salt containing composition, that is to say solution and/or suspension. Preferably, in the precipitation step, the combined mixture, for example a solution and/or suspension, comprising the copper and silicate salts and optionally a base is heated, for example at 50 to 95° C., preferably 70 to 95° C.

The precipitated solid comprising copper and silicate in the dispersion (or slurry) that results from mixing the copper salt containing solution with the silicate salt containing composition, that is to say solution and/or suspension, can be recovered therefrom by filtration. The separated solid may be washed with water, preferably deionized, alkali metal free water, for example in order to remove substantially all alkali metal ions.

Possibly after drying, for example at a temperature in the range of from 80 to 160° C., suitably 100 to 140° C., said precipitated solid, optionally in admixture with an earth alkaline metal silicate salt as described above, is subjected to a temperature in the range of from 150 to 500° C., preferably 200 to 400° C. Preferably, such heat treatment is carried out in the presence of an oxygen gas containing gas, such as air. The latter heat treatment may also be referred to as calcination. Finally, the solid catalyst obtained may be grinded.

In a further embodiment, the catalyst preparation process of the present invention comprises the following steps:

mixing a copper salt containing solution with a silicate salt containing composition, that is to say solution and/or suspension, resulting in a precipitated solid;

subjecting the precipitated solid to a temperature in the range of from 150 to 500° C. resulting in a thermally treated precipitated solid;

mixing the thermally treated precipitated solid with a shaping aid containing suspension;

shaping the mixture thus obtained resulting in shaped bodies; and subjecting the shaped bodies to a temperature in the range of from 150 to 500° C.

The first two steps of the above-mentioned further, second embodiment are identical to the steps of the first embodiment as described above. Therefore, the above description of the first embodiment also applies to these first two steps of the second (further) embodiment. For example, the silicate salt preferably comprises an alkali metal silicate salt, preferably a sodium silicate salt, and/or an earth alkaline metal silicate salt, preferably a calcium silicate salt. More preferably, the silicate salt comprises an alkali metal silicate salt, preferably a sodium silicate salt.

In the above-mentioned further embodiment, the thermally treated precipitated solid, which may be a powder, is mixed with a shaping aid containing suspension. Preferably, the shaping aid containing suspension is an aqueous suspension. The nature of the shaping aid is not essential. Therefore, the shaping aid may be any one of shaping aids which are commonly used in producing shaped, catalyst containing bodies. Examples of shaping aids that may be used in the present invention include silica, graphite, alumina, and so on. Suitably, in the present invention, silica is used as a shaping aid. Said shaping aid (e.g. silica) containing suspension may be a sol, preferably containing shaping aid (e.g. silica) particles having an average size in the range of from 1 to 100 nm, more preferably 5 to 60 nm, most preferably 5 to 30 nm. Said suspension may have any pH. For example, the pH may be below 7 (acidic). However, ammonium stabilised (basic) suspensions may also be applied.

Then the mixture obtained by mixing the thermally treated precipitated solid with the shaping aid containing suspension, is shaped. The resulting shaped bodies may have any form. For example, said mixture may be shaped into a tablet form. Furthermore, any shaping method may be applied, like for example extrusion.

Possibly after drying, for example at a temperature in the range of from 80 to 160° C., suitably 100 to 140° C., said shaped bodies are subjected to a temperature in the range of from 150 to 500° C., preferably 200 to 400° C. Preferably, such heat treatment is carried out in the presence of an oxygen gas containing gas, such as air. The latter heat treatment may also be referred to as calcination. The resulting thermally treated, shaped bodies may suitably be used as catalyst in a fixed bed reactor.

In the above-mentioned further embodiment, it is preferred that after the first heat treatment at a temperature in the range of from 150 to 500° C., an earth alkaline metal silicate salt, preferably a calcium silicate salt, is added before subjecting the shaped bodies to a temperature in the range of from 150 to 500° C. For example, such earth alkaline metal silicate salt may be added before or during the shaping step. However, preferably, such earth alkaline metal silicate salt is mixed with the thermally treated precipitated solid before or during, preferably before, mixing with the shaping aid (e.g. silica) containing suspension.

In a case where such earth alkaline metal silicate salt is added after the first heat treatment, as described above, the silicate salt used in the first (precipitation) step preferably comprises an alkali metal silicate salt, preferably a sodium silicate salt, and/or an earth alkaline metal silicate salt, preferably a calcium silicate salt. More preferably, in such case, said silicate salt comprises said alkali metal silicate salt.

In the above-mentioned further embodiment of the present invention, an earth alkaline metal silicate salt, preferably a calcium silicate salt:
  may be mixed with the copper salt containing solution and/or the silicate salt containing composition before and/or during mixing the copper salt containing solution with the silicate salt containing composition; and/or
  may be mixed with the precipitated solid, resulting from mixing the copper salt containing solution with the silicate salt containing composition, before subjecting the mixture thus obtained to a temperature in the range of from 150 to 500° C.; and/or
  may be mixed with the thermally treated precipitated solid, resulting from subjecting the precipitated solid to a temperature in the range of from 150 to 500° C., before shaping the mixture obtained by mixing the thermally treated precipitated solid with the silica containing suspension, preferably before and/or during mixing the thermally treated precipitated solid with the silica containing suspension.

That is to say, in the above-mentioned further embodiment of the present invention, the earth alkaline metal silicate salt may be added in one or more of the above-described ways. Preferably, the earth alkaline metal silicate salt is added by mixing with the thermally treated precipitated solid, resulting from subjecting the precipitated solid to a temperature in the range of from 150 to 500° C., before shaping the mixture obtained by mixing the thermally treated precipitated solid with the shaping aid containing suspension, preferably before and/or during mixing the thermally treated precipitated solid with the shaping aid containing suspension. Further, the earth alkaline metal silicate salt may be added as an earth alkaline metal silicate salt containing suspension, preferably an aqueous suspension. Further, preferably, the silicate salt from the silicate salt containing composition that is mixed with the copper salt containing solution, comprises an alkali metal silicate salt, preferably a sodium silicate salt. Further, the present invention relates to a copper containing catalyst, obtainable by any one of the processes as described above. Still further, the present invention relates to a use of a copper containing catalyst, obtainable by any one of the processes as described above, in a hydrogenation process. Thus, the present invention also relates to a process for the hydrogenation of methyl phenyl ketone into 1-phenylethanol, wherein the hydrogenation is carried out in the presence of a copper containing catalyst, obtainable by any one of the processes as described above.

The invention is further illustrated by the following Examples.

In addition, it is herewith disclosed that an earth alkaline metal silicate salt, preferably a calcium silicate salt, can be used as catalyst carrier or as carrier or catalyst component for several catalysts, containing one or more transition metals, such as platinum (Pt), silver (Ag), gold (Au), nickel (Ni), copper (Cu), cobalt (Co), vanadium (V), molybdenum (Mo), tungsten (W) and/or rhenium (Re), including oxides of these metals. These catalysts may be produced by impregnation or co-precipitation. The resulting catalysts may be applied for any use, for example in hydrogenation, as already described above, but also in oxidation (for example oxidation of cyclohexanol) or dehydrogenation. Still further, they may be used in removing hydrogen sulfide ($H_2S$) and/or mercury (Hg). In the latter case of Hg removal, the catalyst is preferably first sulfided before use.

Example 1

9149 g of malachite, which is a mineral containing copper carbonate hydroxide of the formula $Cu_2CO_3(OH)_2$, was dissolved in a nitric acid solution. Said nitric acid solution contained 27.5 l of water and 15.1 l of $HNO_3$ and had a concentration of 693.2 g $HNO_3$/l. The resulting solution contained copper nitrate ($Cu(NO_3)_2$).

An alkaline solution was prepared by dissolving 3494 g of sodium hydroxide (NaOH) and 4630 g of sodium carbonate ($Na_2CO_3$) in 47.5 l of water. The molar ratio NaOH:$Na_2CO_3$ was 1.9:1. The concentration of the alkaline solution was adjusted to 170 g NaOH+$Na_2CO_3$/l. Then 1.3 l of a solution containing waterglass, which is sodium silicate of the formula $Na_2SiO_3$, was added to the alkaline solution. The resulting alkaline solution contained 307.7 g $SiO_2$/l and 103.95 g NaOH/l, and was then heated to 80° C.

The copper nitrate containing solution was added to the heated alkaline solution while vigorously stirring the resulting slurry. The temperature during the precipitation was maintained at 80° C. Within about 2 hours, the end of the precipitation was reached at a pH of the slurry of 8.3-8.5. Then at said pH and said temperature and while stirring, aging for a further 60 minutes was carried out. Then the slurry was filtered. The resulting filter cake was washed with deionized water until a $Na_2O$ content lower than 0.3 wt. %, for the residue resulting from annealing a small portion of the filter cake at 800° C., was reached. Then the filter cake was dried in air at 120° C. for 8 hours and subsequently calcined in air at 300° C. for 2 hours. Then the resulting material was grinded into a catalyst powder having a particle size <1.0 mm.

638 g of said catalyst powder was mixed with 16 g of Tylose® which is a binder.

Then 325 ml of an aqueous silica sol suspension (Köstrosol 1540) was slowly added to the mixture thus obtained while mixing (kneading). The water as contained in said suspension was demineralized water. Said silica sol suspension contained 500 g $SiO_2$/l and had a pH below 7. The kneading was continued for 10 minutes and then the kneaded mixture was shaped by extrusion into extrudates having a size of 1.6 mm and a TL shape. Then the extrudates were dried in air at 120° C. for 8 hours and subsequently calcined in air at 300° C. for 2 hours.

Example 2

The procedure of Example 1 was repeated with the exception that the catalyst powder was mixed with 16 g of Tylose® (as in Example 1) and also with 53.2 g of wollastonite. Wollastonite is a mineral containing calcium silicate of the formula $CaSiO_3$.

Comparative Example

Copper carbonate ($CuCO_3$) was thermally treated at 315° C. in an air stream having a flow rate of 250 kg/h, resulting in a copper oxide (CuO) powder. Said powder had a "Residue On Ignition" (ROI; at 800° C. for 2 hours) of 93 wt. % and a BET surface area of 30 $m^2/g$.

1.5 kg of said copper oxide powder was mixed with 0.057 kg of Tylose® (which is a binder), 0.113 kg of wollastonite (which is is a mineral containing calcium silicate of the formula $CaSiO_3$), and 0.193 kg of Sipernat® 50 (which is a silica).

Then 1.007 l of an aqueous silica sol suspension (Köstrosol 1540) was slowly added to the mixture thus obtained while mixing (kneading). The water as contained in said suspension was demineralized water. Said silica sol suspension contained 500 g $SiO_2/l$ and had a pH below 7. The kneading was continued for 10 minutes and then the kneaded mixture was shaped by extrusion into extrudates having a size of 1.6 mm and a TL shape. Then the extrudates were dried in air at 120° C. for 8 hours and subsequently calcined in air at 300° C. for 2 hours.

Hydrogenation Experiments

The catalysts as prepared in Examples 1 and 2 and in the Comparative Example were tested in hydrogenation experiments, more in particular in the hydrogenation of methyl phenyl ketone (MPK; acetophenone) into methyl phenyl carbinol (MPC; 1-phenylethanol).

Before carrying out said hydrogenation experiments, the catalyst was activated in the following way. 25 $cm^3$ of catalyst were placed inside a tubular reactor having a diameter of 2 inch. In a first step, the catalyst was dried at 120° C. for 24 hours in a nitrogen gas containing stream having a GHSV (gas hourly space velocity) of 150 v/vh. Then the reactor was heated up, at a rate of 3 K/min, to 150° C. Then the GHSV of the nitrogen stream was adjusted to 500 v/vh and hydrogen gas was added to said stream, starting with an amount of 0.2 vol. % of hydrogen gas thereby controlling the exothermic reduction reaction. The temperature was stepwise increased to 200° C. Simultaneously, the hydrogen gas proportion was stepwise further increased (and the nitrogen gas proportion decreased) to 100 vol. % of hydrogen gas. The end of the catalyst reduction process was achieved when no further exothermic reaction occurred.

Then the temperature was lowered to 80° C. at which temperature the hydrogenation experiment was carried out by feeding a MPK containing liquid, containing 50.0 wt. % of MPK, 25.0 wt. % of ethylbenzene, 24.7 wt. % of MPC and 0.3 wt. % of styrene, to the reactor, in addition to feeding the hydrogen gas containing stream (trickle flow mode). The reaction pressure was 25 bar. The LHSV (liquid hourly space velocity) for the liquid feed was 1.2 v/vh. The gas-to-liquid ratio was 200:1 v/v.

The conversion and selectivity obtained with each of the catalysts are shown in the table below.

| Catalyst from | Conversion | Selectivity |
| --- | --- | --- |
| Example 1 | 95% | 99% |
| Example 2 | 96% | 99% |
| Comparative Example | 88% | 99% |

From the results in the table above it appears that advantageously, with the catalysts as obtained in accordance with the present invention (Examples 1 and 2) a substantially higher conversion is achieved whereas the selectivity remains the same, when compared to the catalyst obtained in the Comparative Example.

That which is claimed is:

1. A process for preparing a catalyst useful in the hydrogenation of methyl phenyl ketone (MPK) to methyl phenyl carbinol, which process comprises:
   mixing a copper salt containing solution with a composition containing a silicate salt selected from the group consisting of sodium silicate and calcium silicate resulting in a mixture containing a precipitated solid;
   recovering the precipitate solid from the mixture;
   subjecting the recovered precipitated solid to a temperature in the range of from 150 to 500° C. to provide a thermally treated precipitated solid;
   mixing the thermally treated precipitated solid with a silica sol containing silica particles having an average size in the range of from 1 to 100 nm to provide a second mixture;
   forming the second mixture into a shaped body; and
   drying the shaped body at a temperature in the range of from 80 to 160° C. followed by subjecting the shaped body to a temperature in the range of from 150 to 500° C. to yield the catalyst.

2. The process according to claim 1, wherein the silicate salt is sodium silicate.

3. The process according to claim 2, wherein the catalyst comprises an amount of copper in the range of from 40 to 95 wt %, calculated as copper (II) oxide (CuO) based on the total weight of the catalyst.

4. The process according to claim 3, further comprising:
   adding a base to the mixture of copper salt containing solution and silicate salt to provide for a pH of 7 or greater; and
   heating the mixture to a temperature in the range of from 50 to 95° C.

5. A process for preparing a catalyst, wherein the process comprises:
   mixing a copper salt-containing solution with an alkali metal silicate salt resulting in a precipitated solid;
   mixing the mixture with an alkaline earth metal silicate salt to provide a mixture; and
   subjecting the mixture to a temperature in the range of from 150 to 500° C.

6. The process according to claim 5, wherein the catalyst comprises an amount of copper in the range of from 40 to 95 wt %, calculated as copper (II) oxide (CuO) based on the total weight of the catalyst.

7. The process according to claim 6, further comprising:
   mixing a base with the copper salt-containing solution and alkali metal silicate salt that results in the precipitate solid; and
   heating the resulting mixture of copper salt-containing solution, alkali metal silicate salt, and base at a temperature in the range of from 50 to 95° C.

8. The process according to claim 7, wherein the alkali metal silicate salt is a sodium silicate salt and the alkaline earth metal silicate salt is a calcium silicate salt.

9. A process for preparing a catalyst, wherein the process comprises:
mixing either an alkaline earth metal silicate salt or a silicate salt-containing composition with a precipitated solid, wherein the precipitated solid results from mixing a copper salt containing solution with a first silicate salt-containing composition, to provide a mixture; and
subjecting the mixture to a temperature in the range of from 150 to 500° C.

10. The process according to claim 9, wherein the first silicate salt of the silicate salt containing composition is an alkali metal silicate salt.

11. The process according to claim 10, wherein the precipitated solid is thermally treated at a temperature in the range of from 150 to 500° C. before mixing with the alkaline earth metal silicate salt or the first silicate salt-containing composition.

12. The process according to claim 10, further comprising:
mixing a second alkaline earth metal silicate salt with the copper salt containing solution and the first silicate salt containing composition in providing the mixture.

13. The process according to claim 12, wherein the first silicate salt of the silicate salt-containing composition is an alkali metal silicate salt.

14. The process according to claim 10, further comprising:
mixing a second alkaline earth metal silicate salt with the precipitated solid before the thermal treatment of the precipitated solid.

15. The process according to claim 10, further comprising:
mixing a second alkaline earth metal silicate salt and a shaping aid with the thermally treated precipitated solid to provide a second mixture;
forming the second mixture into a shaped body; and
drying the shaped body at a temperature in the range of from 80 to 160° C. followed by subjecting the shaped body to a temperature in the range of from 150 to 500° C. to yield the catalyst.

16. The process according to claim 10, wherein the catalyst comprises an amount of copper in the range of from 40 to 95 wt %, calculated as copper (II) oxide (CuO) based on the total weight of the catalyst.

17. The process according to claim 16, further comprising:
activating the catalyst by contacting it with hydrogen gas to thereby provide an exothermic reduction reaction of the catalyst to provide an activated catalyst.

18. The process according to claim 17, wherein the alkali metal silicate salt is a sodium silicate salt, the alkaline earth metal silicate salt is a calcium silicate salt, and the silicate salt of the silicate salt-containing composition is a sodium silicate salt.

19. A process for preparing an activated catalyst, which process comprises:
mixing a copper salt containing solution with a silicate salt containing composition resulting in a precipitated solid;
subjecting the precipitated solid to a temperature in the range of from 150 to 500° C. resulting in a thermally treated precipitated solid;
mixing the thermally treated precipitated solid with a shaping aid containing suspension;
shaping the mixture thus obtained resulting in shaped bodies; and
subjecting the shaped bodies to a temperature in the range of from 150 to 500° C. to provide a catalyst; and
activating the catalyst by contacting it with hydrogen gas to thereby provide an exothermic reduction reaction of the catalyst to provide the activated catalyst.

20. The process according to claim 19, wherein the silicate salt is either an alkali metal silicate salt or an alkaline earth metal silicate salt.

21. The process according to claim 20, wherein the silicate salt comprises an alkali metal silicate salt.

22. The process according to claim 21, wherein the catalyst comprises an amount of copper in the range of from 40 to 95 wt %, calculated as copper (II) oxide (CuO) based on the total weight of the catalyst.

23. The process according to claim 22, further comprising:
mixing a base with the copper salt-containing solution and alkali metal silicate salt that results in the precipitate solid; and
heating the resulting mixture of copper salt-containing solution, alkali metal silicate salt, and base at a temperature in the range of from 50 to 95° C.

* * * * *